(12) United States Patent
Kurita et al.

(10) Patent No.: US 8,183,206 B2
(45) Date of Patent: May 22, 2012

(54) DRUGS COMPRISING COMBINATION OF ANTITHROMBOTIC AGENT WITH PYRAZOLONE DERIVATIVE

(75) Inventors: Katsumi Kurita, Tokyo (JP); Tadashi Tanaka, Tokyo (JP); Masahiko Tanaka, Tokyo (JP); Jyunichi Eguchi, Tokyo (JP); Satoshi Yuki, Tokyo (JP); Narihiko Yoshii, Tokyo (JP)

(73) Assignee: Mitsubishi Tanabe Pharma Corporation, Osaka (JP)

( * ) Notice: Subject to any disclaimer, the term of this patent is extended or adjusted under 35 U.S.C. 154(b) by 1254 days.

(21) Appl. No.: 10/489,507

(22) PCT Filed: Sep. 13, 2002

(86) PCT No.: PCT/JP02/09425
§ 371 (c)(1),
(2), (4) Date: Sep. 3, 2004

(87) PCT Pub. No.: WO03/024445
PCT Pub. Date: Mar. 27, 2003

(65) Prior Publication Data
US 2005/0009896 A1 Jan. 13, 2005

(30) Foreign Application Priority Data

Sep. 14, 2001 (JP) ................. 2001-279645
Nov. 29, 2001 (JP) ................. 2001-365032

(51) Int. Cl.
*A61K 38/36* (2006.01)
*A61K 31/4152* (2006.01)
(52) U.S. Cl. ................... 514/14.9; 514/407
(58) Field of Classification Search .......... 514/49, 514/161, 94.64, 404, 183, 18, 406, 14.9, 514/407
See application file for complete search history.

(56) References Cited

U.S. PATENT DOCUMENTS 4,857,542 A 8/1989 Nishi et al.
5,827,832 A * 10/1998 Sandage et al. ............ 514/49

FOREIGN PATENT DOCUMENTS

EP 0208874 A1 1/1987

OTHER PUBLICATIONS

Vippagunta et al (Advanced Drug Delivery Reviews 2001; 48: 3-26).*
Uchiyama (Internal Medicine 2006; 45: 493-494).*
WebMD ([online], www.webmd.com [Retrieved from the Internet on Apr. 30, 2009]. <URL: http://www.webmd.com/alzheimers/tc/alzheimers-disease-cause).*
Asahi et al. (Journal of Cerebral Blood Flow and Metabolism, vol. 20, pp. 452-457; 2000).*
Suzuki et al. (Folia Pharmacol. Jpn., vol. 116, pp. 379-384; 2000).*
Swigris et al. (J Vasc Surg, vol. 29, No. 5, abstract; 1999).*
Albers, *The American Journal of Cardiology*, 75(6): 34B-38B (Feb. 23, 1995).
Budavari et al. (Ed.), *The Merck Index*, 11$^{th}$ edition, p. 123 (entry 804: Argatroban) and pp. 1104-1105 (entry 6935: Ozagrel) (1989).
Jin et al., *Neuroscience Research*, 43(1): 75-79 (May 2002).
Watanabe et al., "Drug interaction between radical scavenger, 3-methyl-1-phenyl-2-pyrazolin-5-one (MCI-186), and stroke-medicating agents," *Database EMBASE Online*: Accession No. EMB-1998020759 (1997), with abstract of *Japanese Pharmacology and Therapeutics*, 25, suppl. 7: 199-208 (1997).
Beers et al. (Ed.), *The Merck Manual of Diagnosis and Therapy*, 17$^{th}$ edition, pp. 1420-1424 (1999).
Budavari et al. (Ed.), *The Merck Index*, 12$^{th}$ edition, pp. 131-132 (entry 816: Argatroban) and p. 1198 (entry 7115: Ozagrel)(1996).
Shiqi et al., "Clinical Observation of Noval [sic] Antithrombotic-drug Lumbrukinase for the Treatment of Ischemic Cerebrovascular Disease," *Chinese Journal of Neurology*, No. 04 (1993).

* cited by examiner

*Primary Examiner* — Phyllis G. Spivack
*Assistant Examiner* — Nelson C Blakely, III
(74) *Attorney, Agent, or Firm* — Leydig, Voit & Mayer, Ltd.

(57) ABSTRACT

It is intended to provide drugs for treating ischemic diseases which are safe and have little side effects. Namely, drugs having a combination of an antithrombotic agent and a pyrazolone derivative defined in the description or its pharmaceutically acceptable salt.

6 Claims, No Drawings

DRUGS COMPRISING COMBINATION OF ANTITHROMBOTIC AGENT WITH PYRAZOLONE DERIVATIVE

TECHNICAL FIELD

This invention relates to a drug comprising a combination of antithromotic agent with a pyrazolone derivative. In more detail, the present invention relates to the aforementioned combined drug which is useful for the remedy and/or prevention of various ischemic diseases.

BACKGROUND ART

As the remedial agent for the acute cerebral infarction, an antithrombotic agent (a thrombolytic agent, an anticoagulant, a platelet aggregation inhibitory agent) has been used hereinbefore. The remedy using such antithrombotic agent was given the priority to the treatment for the thrombus in blood vessel and the improvement of circulation. The known antithrombotic agent includes a tissue plasmigogen activator (hereinafter sometimes referred to as t-PA), a urokinase (UK), heparin, argatroban, ozagral sodium, aspirin and ticlopidine and the like.

However, if the antithrombotic agent is administered in large quantities or the administration of the antithrombotic agent is delayed, the conditions of the patient become worse by occurrence of the adverse effect of cerebral hemorrhage. Consequently, it cannot be said that there are few subjects to be solved.

Edaravone (3-methyl-1-phenyl-2-pyrazolin-5-one), recently developed radical scavenger which was claimed in Japanese Patent Examined Publication (Kokoku) No. Hei. 4-35128 exhibits a free radical scavenging activity and an inhibiting activity against lipid peroxidation in cell membranes and the like. According to such activities, edaravone protects the nerve cell at the ischemic penumbra, and is able to keep the ischemic disorder to a minimum. The characteristics of edaravone includes no influence to the coagulation of blood and the aggregation of platelet and the like, and few hemorrhagic adverse effects.

DISCLOSURE OF THE INVENTION

The subject to be solved of the present invention is to provide a drug for the remedy and/or prevention of ischemic diseases with less adverse effect, safety and having high clinical effects.

The present inventors have conducted various investigations to heighten the clinical effects accompanied with more high safety in the treatment of the aforementioned antithrombotic agent and found that the combination of the antithrombotic agent with a pyrazolone derivative of the formula (I) can provides the drug for the remedy and/or prevention of ischemic diseases with less adverse effect, safety and having high clinical effects, and then completed the present invention.

Namely, the present invention provides a drug comprising a combination of an antithrombotic agent with a pyrazolone derivative of the following formula (I), or a pharmaceutically acceptable salt thereof, or a hydrate or solvate thereof.

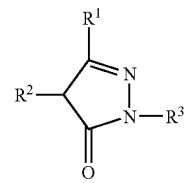

(wherein $R^1$ represents hydrogen atom, an aryl group, an alkyl group having 1 to 5 carbon atoms or an alkoxycarbonylalkyl group having 3 to 6 carbon atoms in total; $R^2$ represents hydrogen atom, an aryloxy group, an arylmercapto group, an alkyl group having 1 to 5 carbon atoms or a hydroxyalkyl group having 1 to 3 carbon atoms; or $R^1$ and $R^2$ is coupled together to form an alkylene group having 3 to 5 carbon atoms; and $R^3$ represents hydrogen atom, an alkyl group having 1 to 5 carbon atoms, a cycloalkyl group having 5 to 7 carbon atoms, a hydroxyalkyl group having 1 to 3 carbon atoms, benzyl group, a naphthyl group or phenyl group, or a phenyl group substituted with 1 to 3 substituents, which may be the same or different and selected from the group consisting of an alkyl group having 1 to 5 carbon atoms, an alkoxy group having 1 to 5 carbon atoms, a hydroxyalkyl group having 1 to 3 carbon atoms, an alkoxycarbonyl group having 2 to 5 carbon atoms in total, an alkylmercapto group having 1 to 3 carbon atoms, an alkylamino group having 1 to 4 carbon atoms, a dialkylamino group having 2 to 8 carbon atoms in total, a halogen atom, trifluoromethyl group, carboxyl group, cyano group, hydroxyl group, nitro group, amino group and acetamido group).

Further, the present invention provides a combined drug to administer the antithrombotic agent and the pyrazolone derivative of the aforementioned formula (I), simultaneously, separately or sequentially.

The preferable examples of antithrombotic agent are a thrombolytic agent, an anticoagulant, and a platelet aggregation inhibitory agent. The preferable example of thrombolytic agents is t-PA, the preferable example of anticoagulants is antithrombin agent, and the preferable example of platelet aggregation inhibitory agents is a thromboxane synthetase inhibitor. The concrete example of antithrombin agents is, for example, (2R, 4R)$_4$-methyl-1-[N$^2$-((RS)-3-methyl-1,2,3,4-tetrahydro-8-quinolinesulfonyl)-L-arginyl]-2-piperidinecarboxylic acid monohydrate (non-proprietary name: argatroban):

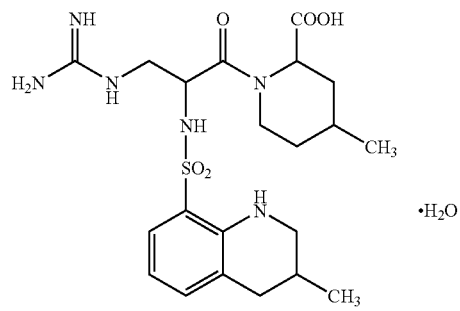

and the concrete example of thromboxane synthetase inhibitors is sodium (E)-[p-(1H-imidazol-1-yl)phenyl]-2-propenoate (non-proprietary name: ozagrel sodium):

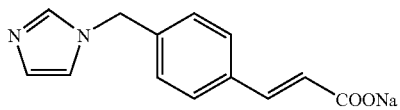

Particularly preferable example of the antithrombotic agent of the present invention is t-PA, (2R, 4R)-4-methyl-1-[$N^2$-((RS)-3-methyl-1,2,3,4-tetrahydro-8-quinolinesulfonyl)-L-arginyl]-2-piperidinecarboxylic acid monohydrate, and sodium (E)-[p-(1H-imidazol-1-yl)phenyl]-2-propenoate. Further, more preferably, (2R, 4R)-4-methyl-1-[$N^2$-((RS)-3-methyl-1,2,3,4-tetrahydro-8-quinolinesulfonyl)-L-arginyl]-2-piperidinecarboxylic acid monohydrate, and sodium (E)-[p-(1H-imidazol-1-yl) phenyl]-2-propenoate can be exemplified.

The pyrazolone derivative of the formula (I) is preferably 3-methyl-1-phenyl-2-pyrazolin-5-one.

The combined drugs of the present invention can be preferably used for the remedy and/or prevention of ischemic diseases. Specific examples of such ischemic diseases include various ischemic diseases or various diseases caused thereby, more specifically, various cerebral diseases, for example, cerebrovascular disorders such as cerebral infraction and stroke, impairment of brain functions due to these cerebrovascular disorders, vascular dementia, and age-related damage to cerebrovascular tissue; various heart diseases caused by myocardial ischemia such as myocardial infarction and cardiac failure; and various peripheral circulatory disorders. Preferred examples include nerve symptoms, daily behavior problems and functional disturbances, each in the acute stage of cerebral infarction; neurological symptoms (motor paralysis) in acute cerebral thrombosis (excluding lacunar infarction) within 48 hours from onset, disturbances against activities of daily living (walking, standing, sustaining the sitting position, eating); and dyskinesia associated with cerebral thrombosis (acute stage).

Moreover, the present invention provides a remedial agent and/or preventive agent for ischemic diseases by administering the antithrombotic agent and the pyrazolone derivative of the aforementioned formula (I) or a pharmaceutically acceptable salt thereof, or a hydrate or solvate thereof, simultaneously, separately or sequentially.

Furthermore, the present invention provides an agent for improving the function prognosis after the administration of an antithrombotic agent, which contains the pyrazolone derivative of the aforementioned formula (I) or a pharmaceutically acceptable salt thereof, or a hydrate or solvate thereof.

Another aspect of the present invention provides a method of treating and/or preventing ischemic diseases comprising administering a pharmacologically effective amount of a antithrombotic agent and a pharmacologically effective amount of a pyrazolone derivative of the aforementioned formula (I) or a pharmaceutically acceptable salt thereof, or a hydrate or solvate thereof to mammals inclusive of human beings, simultaneously, separately or sequentially.

Further, another aspect of the present invention provides a use of a antithrombotic agent and a pyrazolone derivative of the aforementioned formula (I) or a pharmaceutically acceptable salt thereof, or a hydrate or solvate thereof for manufacturing a combined drug.

BEST MODES FOR CARRYING OUT THE INVENTION

Followings are the detailed explanations on the modes for carrying out the present invention.

The combined drugs of the present invention contain an antithrombotic agent and a pyrazolone derivative of the formula (I) defined in the present specification or a pharmaceutically acceptable salt thereof.

The antithrombotic agent used in the present invention includes a tissue plasminogen activator (t-PA), a urokinase (UK), heparin, argatroban, ozagrel sodium, aspirin, ticlopidine and the like and the present invention is construed not to limited by them. The particularly preferable antithrombotic agent includes a tissue plasminogen activator (t-PA). Other particularly preferable antithrombotic agents include antithrombin agent and/or a thromboxane synthetase inhibitory agent and more concretely (2R, 4R)-4-methyl-1-[$N^2$-((RS)-3-methyl-1,2,3,4-tetrahydro-8-quinolinesulfonyl)-L-arginyl]-2-piperidinecarboxylic acid monohydrate (argatroban) and/or sodium (E)-[p-(1H-imidazol-1-yl) phenyl]-2-propenoate (ozagrel sodium).

The compound of formula (I) used in the present invention may have the following chemical structures of formulae (I') and (I''). Consequently, the active ingredient of the present invention embraces the compounds of formulae (I') and (I'')

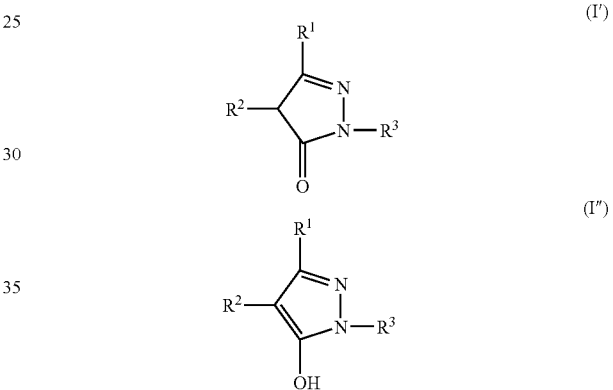

In the formula (I), the aryl group in the definition of $R^1$ includes phenyl group and a phenyl group substituted by a substituent such as methyl group, butyl group, methoxy group, butoxy group, chlorine atom and hydroxyl group and the like.

The alkyl group having 1 to 5 carbon atoms in the definition of $R^1$, $R^2$ and $R^3$ includes methyl group, ethyl group, propyl group, isopropyl group, butyl group, isobutyl group, sec-butyl group, tert-butyl group, pentyl group and the like.

The alkoxycarbonylalkyl group having 3 to 6 carbon atoms in total in the definition of $R^1$ includes methoxycarbonylmethyl group, ethoxycarbonylmethyl group, propoxycarbonylmethyl group, methoxycarbonylethyl group, methoxycarbonylpropyl group and the like.

In the definition of $R^2$, the aryloxy group is phenoxy group, p-methylphenoxy group, p-methoxyphenoxy group, p-chlorophenoxy group, p-hydroxyphenoxy group and the like, and the arylmercapto group includes phenylmercapto group, p-methyl phenylmercapto group, p-methoxyphenylmercapto group, p-chlor phenylmercapto group, p-hydroxyphenylmercapto group and the like.

The hydroxyalkyl group having 1 to 3 carbon atoms in the definition of $R^2$ and $R^3$ includes hydroxymethyl group, 2-hydroxyethyl group, 3-hydroxypropyl group and the like. The cycloalkyl group having 5 to 7 carbon atoms in the definition of $R^3$ is cyclopentyl group, cyclohexyl group, cycloheptyl group and the like.

In the substituent of the phenyl group in the definition of $R^3$, the alkoxy group having 1 to 5 carbon atoms includes methoxy group, ethoxy group, propoxy group, isopropoxy group, butoxy group, pentyloxy group and the like, the alkoxycarbonyl group having 2 to 5 carbon atoms in total includes methoxycarbonyl group, ethoxycarbonyl group, propoxycarbonyl group, butoxycarbonyl group and the like, the alkylmercapto group having 1 to 3 carbon atoms includes methylmercapto group, ethylmercapto group, propylmercapto group and the like, the alkylamino group having 1 to 4 carbon atoms includes methylamino group, ethylamino group, propylamino group, butylamino group and the like, and the dialkylamino group having 2 to 8 carbon atoms in total includes dimethylamino group, diethylamino group, dipropylamino group, dibutylamino group and the like.

The Examples of the compounds of formula (I) used in the present invention include, for example, the following compounds:

3-Methyl-1-phenyl-2-pyrazolin-5-one,
3-Methyl-1-(2-methylphenyl)-2-pyrazolin-5-one,
3-Methyl-1-(3-methylphenyl)-2-pyrazolin-5-one,
3-Methyl-1-(4-methylphenyl)-2-pyrazolin-5-one,
3-Methyl-1-(3,4dimethylphenyl)-2-pyrazolin-5-one,
1-(4-Ethylphenyl)-3-methyl-2-pyrazolin-5-one,
3-Methyl-1-(4-propylphenyl)-2-pyrazolin-5-one,
1-(3-Butylphenyl)-3-methyl-2-pyrazolin-5-one,
1-(3-Trifluoromethylphenyl)-3-methyl-2-pyrazolin-5-one,
1-(4-Trifluoromethylphenyl)-3-methyl-2-pyrazolin-5-one,
1-(2-Methoxyphenyl)-3-methyl-2-pyrazolin-5-one,
1-(3-Methoxyphenyl)-3-methyl-2-pyrazolin-5-one,
1-(4-Methoxyphenyl)-3-methyl-2-pyrazolin-5-one,
1-(3,4-Dimethoxyphenyl)-3-methyl-2-pyrazolin-5-one,
1-(4-Ethoxyphenyl)-3-methyl-2-pyrazolin-5-one,
3-Methyl-1-(4-propoxyphenyl)-2-pyrazolin-5-one,
1-(4-Butoxyphenyl)-3-methyl-2-pyrazolin-5-one,
1-(2-Chlorophenyl)-3-methyl-2-pyrazolin-5-one,
1-(3-Chlorophenyl)-3-methyl-2-pyrazolin-5-one,
1-(4-Chlorophenyl)-3-methyl-2-pyrazolin-5-one,
1-(3,4-Dichlorophenyl)-3-methyl-2-pyrazolin-5-one,
1-(4-Bromophenyl)-3-methyl-2-pyrazolin-5-one,
1-(4-Fluorophenyl)-3-methyl-2-pyrazolin-5-one,
1-(3-Chloro-4-methylphenyl)-3-methyl-2-pyrazolin-5-one,
1-(3-Methylmercaptophenyl)-3-methyl-2-pyrazolin-5-one,
1-(4-Methylmercaptophenyl)-3-methyl-2-pyrazolin-5-one,
4-(3-methyl-5-oxo-2-pyrazolin-1-yl)benzoic acid,
1-(4-Ethoxycarbonylphenyl)-3-methyl-2-pyrazolin-5-one,
1-(4-Nitrophenyl)-3-methyl-2-pyrazolin-5-one,
3-Ethyl-1-phenyl-2-pyrazolin-5-one,
1-Phenyl-3-propyl-2-pyrazolin-5-one,
1,3-Diphenyl-2-pyrazolin-5-one,
1-Phenyl-3-(p-tolyl)-2-pyrazolin-5-one,
1-(4-Methoxyphenyl)-3-phenyl-2-pyrazolin-5-one,
1-(4-Chlorophenyl)-3-phenyl-2-pyrazolin-5-one,
3,4-Dimethyl-1-phenyl-2-pyrazolin-5-one,
4-Isobutyl-3-methyl-1-phenyl-2-pyrazolin-5-one,
4-(2-Hydroxyethyl)-3-methyl-1-phenyl-2-pyrazolin-5-one,
3-Methyl-4-phenoxy-1-phenyl-2-pyrazolin-5-one,
3-Methyl-4-phenylmercapto-1-phenyl-2-pyrazolin-5-one,
3,3',4,5,6,7-Hexahydro-2-phenyl-2H-indazol-3-one,
3-(Ethoxycarbonylmethyl)-1-phenyl-2-pyrazolin-5-one,
1-Phenyl-2-pyrazolin-5-one,
3-Methyl-2-pyrazolin-5-one,
1,3-Dimethyl-2-pyrazolin-5-one,
1-Ethyl-3-methyl-2-pyrazolin-5-one,
1-Butyl-3-methyl-2-pyrazolin-5-one,
1-(2-Hydroxyethyl)-3-methyl-2-pyrazolin-5-one,
1-Cyclohexyl-3-methyl-2-pyrazolin-5-one,
1-Benzyl-3-methyl-2-pyrazolin-5-one,
1-(α-Naphthyl)-3-methyl-2-pyrazolin-5-one,
1-Methyl-3-phenyl-2-pyrazolin-5-one,
3-Methyl-1-(4-methylphenyl)-2-pyrazolin-5-one,
1-(4-Butylphenyl)-3-methyl-2-pyrazolin-5-one,
1-(4-Methoxyphenyl)-3-methyl-2-pyrazolin-5-one,
1-(4-Butoxyphenyl)-3-methyl-2-pyrazolin-5-one,
1-(4-Chlorophenyl)-3-methyl-2-pyrazolin-5-one,
1-(4-Hydroxyphenyl)-3-methyl-2-pyrazolin-5-one,
1-(3,4-Dihydroxyphenyl)-3-methyl-2-pyrazolin-5-one,
1-(2-Hydroxyphenyl)-3-methyl-2-pyrazolin-5-one,
1-(3-Hydroxyphenyl)-3-methyl-2-pyrazolin-5-one,
1-(4-Hydroxyphenyl)-3-methyl-2-pyrazolin-5-one,
1-(3,4-Dihydroxyphenyl)-3-methyl-2-pyrazolin-5-one,
1-(4-Hydroxyphenyl)-3-phenyl-2-pyrazolin-5-one,
1-(4-Hydroxymethylphenyl)-3-methyl-2-pyrazolin-5-one,
1-(4-Aminophenyl)-3-methyl-2-pyrazolin-5-one,
1-(4-Methylaminophenyl)-3-methyl-2-pyrazolin-5-one,
1-(4-Ethylaminophenyl)-3-methyl-2-pyrazolin-5-one,
1-(4-Butylaminophenyl)-3-methyl-2-pyrazolin-5-one,
1-(4-Dimethylaminophenyl)-3-methyl-2-pyrazolin-5-one,
1-(Acetoamidophenyl)-3-methyl-2-pyrazolin-5-one, and
1-(4-Cyanophenyl)-3-methyl-2-pyrazolin-5-one.

As the active ingredient of the drug of the present invention, a physiologically acceptable salt as well as a free form of the compound of formula (I) can be used. Such physiologically acceptable salt includes a salt with a mineral acid such as hydrochloric acid, sulfuric acid, hydrobromic acid, phosphoric acid and the like; a salt of an organic acid such as methanesulfonic acid, p-toluenesulfonic acid, benzenesulfonic acid, acetic acid, glycolic acid, glucuronic acid, maleic acid, fumaric acid, oxalic acid, ascorbic acid, citric acid, salicylic acid, nicotinic acid, tartaric acid and the like; a salt with an alkaline metal such as sodium, potassium and the like, and a salt with an amine such as ammonia, tris(hydroxymethyl)aminomethane, N,N-bis(hydroxyethyl)piperazine, 2-amino-2-methyl-1-propanol, ethanolamine, N-methylglutamine, L-glutamine and the like. Further, a salt with an amino acid such as glycine can be used.

The active ingredient of the drug of the present invention can be used as a hydrate of the compound of the aforementioned formula (I) or a physiologically acceptable salt thereof, and a solvate of the compound of the aforementioned formula (I) or a physiologically acceptable salt thereof. A type of the solvent used to form a solvate is not specifically limited. For example, methanol, ethanol, ether, dioxane, tetrahydrofuran can be exemplified. In case that the compounds of the aforementioned formula (I) have one or more asymmetric carbons based on the type of the substituent, there may exist a stereoisomer such as an optical isomer or a diastereoisomer. As the active ingredient of the drug of the present invention, a stereoisomer in a pure form, any mixture of stereoisomers, a racemate and the like may also be used.

The compounds of formula (I) used in the present invention are known compounds and disclosed, for example, in Japanese Patent Examined Publication (Kokoku) No. Hei. 5-31523, Japanese Patent Examined Publication (Kokoku) No. Hei. 5-35128 and the like.

The dose of the antithrombotic agent used in the present invention is usually 0.01 to 100 mg/kg per day, preferably 0.1 to 10 mg/kg per day for the parenteral administration, and 1 to 1,000 mg/kg per day, preferably 0.5 to 50 mg/kg per day for the oral administration. The aforementioned dose can be preferably administered once to three times a day. The dose mentioned above may be suitably varied depending upon the age, and the severity and condition of the diseases.

The dose of the pyrazolone derivative of the formula (I) used in the present invention is usually 0.01 to 100 mg/kg per day, preferably 0.1 to 10 mg/kg per day for the parenteral administration, and 1 to 1,000 mg/kg per day, preferably 0.5 to 50 mg/kg per day for the oral administration. The aforementioned dose can be preferably administered once to three times a day. The dose mentioned above may be suitably varied depending upon the age, and the severity and condition of the diseases.

The combined drug of the present invention may be administered separately by formulating each of the antithrombotic agents and the pyrazolone derivatives of formula (I) into each of drugs. The antithrombotic agent and the pyrazolone derivative of formula (I) can be administered simultaneously, separately or sequentially. The antithrombotic agent and the pyrazolone derivative of formula (I) can be also administered by formulating them into a single formulation.

In the present invention, the antithrombotic agent and the pyrazolone derivative of formula (I), a physiologically acceptable salt thereof, or a hydrate or solvate thereof can be administered themselves, but usually and preferably administered by preparing a pharmaceutical composition containing the aforementioned substance as the active ingredient and a pharmacologically and pharmaceutically acceptable additive.

Such pharmacologically and pharmaceutically acceptable additive include, for example, an excipient, a disintegrator or a disintegration adjuvant agent, a binder, a lubricant, a coating agent, a pigment, a diluent, a base, a solvent or a solubilizer, an isotonic agent, a pH adjusting agent, a stabilizer, a propellant, and an adhesive.

As the additives of the pharmaceutical composition suitable to the oral administration, for example, an excipient such as glucose, lactose, D-mannitol, starch, or crystalline cellulose and the like; a disintegrator or a disintegration adjuvant agent such as carboxymethylcellulose, starch, or calcium carboxymethylcellulose and the like; a binder such as hydroxypropylcellulose, hydroxypropylmethylcellulose, polyvinylpyrrolidone, or gelatin and the like; a lublicant such as magnesium stearate or talc and the like; a coating agent such as hydroxypropylmethylcellulose, sucrose, polyethyleneglycol, or titanium oxide and the like; or a base such as vaseline, liquid paraffin, polyethyleneglycol, gelatin, kaolin, glycerin, purified water or a hard fat can be used.

For a pharmaceutical composition suitable for an injection or a drip infusion, there can be used an additive, for example, a solvent or a solubilizer such as distilled water for injection, physiological saline or propylene glycol that can constitute an aqueous injection or an injection that is dissolved when used; an isotonic agent such as glucose, sodium chloride, D-mannitol, glycerin and the like; or a pH adjusting agent such as an inorganic acid, an organic acid, an inorganic base or an organic base and the like.

The form of the drug of the present invention is not specifically limited, and may be any of the various forms that can be applied to the person skilled in the art. As the drug appropriate for oral administration, for example, tablets, powders, granules, hard gelatin capsules, suppositories, or troches and the like can be prepared by using solid additives for pharmaceutical preparation, and for example, syrups, emulsions, soft gelatin capsules and the like can be prepared by using liquid additives for pharmaceutical preparation. As the pharmaceutical preparation suitable for parenteral administration, injections, drip infusions, inhalants, percutaneous absorbents, trans-mucosal absorbents and the like can be prepared. As a protective agent for the brain (infusion drip) containing the compound of the aforementioned formula (I) as the active ingredient has already been clinically used (under non-proprietary name: "Edaravone", and the commercial name: "Radicut"; manufactured and distributed by Mitsubishi Pharma Corporation), the aforementioned commercially available drug can be used as it is as the pyrazolone derivative of formula (I) for the combined drug of the present invention.

The present invention will be explained in more detail by the following examples. The scope of the present invention is not limited by the following examples.

In the following examples, GRTPA™ (manufactured and distributed by Mitsubishi Pharma Corporation), XANBON™ (manufactured and distributed by Kissei Pharmaceutical Co., Ltd.) and NOVASTAN™ (manufactured and distributed by Mitsubishi Pharma Corporation) can be used as t-PA, ozagrel sodium, argatroban, respectively, but any pharmaceutical preparations containing t-PA, ozagrel sodium, argatroban as the active ingredient which are regardless of the manufacturing or distributing company can be used.

EXAMPLE

Synthetic Example

Synthesis of 3-methyl-phenyl-2-pyrazolin-5-one (Hereinafter Referred to as Edaravone)

13.0 g of ethyl acetacetate and 10.8 g of phenylhydrazine were added to 50 ml of ethanol, and the mixture was stirred under reflux for 3 hours. After cooling the reaction solution by standing, the precipitated crystals were collected by filtration and recrystallized from ethanol to give 11.3 g of the title compound as a colorless crystal.

Example 1

Test Method

Via a cannula inserted into the femoral vein of each Wistar rat anesthetized with urethane (1.2 g/kg, i.p.), 1 mg/kg (1 mg=580000 IU; 4 mL/kg, 1 mL/hr) of physiological saline or t-PA was constantly infused. Fifty five minutes after the constant fusion was started, 3 mg of edaravone (3-methyl-1-phenyl-2-pyrazolin-5-one) or physiological saline was administered intravenously. Five minutes after that, the tail was transected at 2 mm from its tip immediately by using a razor. Every 15 seconds, the blood from the tail was blotted with a filter paper and the time until bleeding ceased was measured for up to 30 minutes.

(Test Results)

The results of the influence of t-PA on the bleeding time are shown in Table 1 (all the numerical values in this table indicate average±S.E.).

It has been recognized that compared with the control group (physiological saline), the t-PA-administered group prolonged the bleeding time significantly. The t-PA- and edaravone-administered group did not have a significant influence on the bleeding time, compared with the edaravone-administered group. From this, it is apparent that edaravone can be used in combination with t-PA without causing any side effects.

TABLE 1

Influence of t-PA on the bleeding time

| Medicament | Number of cases | Bleeding time (min) |
|---|---|---|
| Control | 10 | 9.33 ± 2.36 |
| Edaravone, 3 mg/kg | 10 | 11.55 ± 2.31 |
| t-PA, 1 mg/kg (1 mg = 580000 IU) | 10 | 17.70 ± 2.85* |
| Edaravone, 3 mg/kg + t-PA, 1 mg/kg | 10 | 15.40 ± 2.77 |

*P < 0.05 (t-test, vs control)

Example 2

Test Method

As shown in Table 2, 37 patients diagnosed as cerebral infarction were classified and administered with a medicament. Administration amount and method are shown below.

Sodium ozagrel: 80 mg of sodium ozagrel was dissolved in an adequate amount of an electrolyte solution or carbohydrate solution and the resulting solution was intravenously administered constantly for 2 weeks, twice daily, that is, in the morning and evening, each over 2 hours.

Argatroban: For the first two days, 60 mg/120 ml of argatroban was diluted with an adequate amount of a transfusion fluid and the resulting solution was intravenously infused constantly over 24 hours. For the following 5 days, 10 mg/20 ml of argatroban was diluted with an adequate amount of a transfusion fluid and the resulting solution was intravenously infused twice daily, that is, in the morning and evening, each over 3 hours.

Sodium ozagrel+edaravone: 80 mg of sodium ozagrel was dissolved in an adequate amount of an electrolyte solution or carbohydrate solution and the resulting solution was intravenously administered constantly for 2 weeks, twice daily, that is, in the morning and evening, each over 2 hours. At the same time, 30 mg/20 ml of edaravone was diluted with an adequate amount of physiological saline and the resulting solution was intravenously infused for 2 weeks, twice daily, that is, in the morning and evening, each over 20 minutes.

Argatroban+edaravone: For the first two days, 60 mg/120 ml of argatroban was diluted with an adequate amount of a transfusion fluid and the resulting solution was intravenously infused constantly over 24 hours. For the following 5 days, 10 mg/20 ml of argatroban was diluted with an adequate amount of a transfusion fluid and the resulting solution was intravenously infused twice daily, that is, in the morning and evening, each over 3 hours; and at the same time, 30 mg/20 ml of edaravone was diluted with an adequate amount of physiological saline and the resulting solution was intravenously infused for 2 weeks twice daily, that is, in the morning and evening, each over 30 minutes.

(Test Results)

On the leaving day of the hospital within 1 month after the administration was started (after one month when the patient was in hospital), evaluation results of the function prognosis in accordance with the modified ranking scale are shown in Table 2.

TABLE 2

| | Grade | | | | | | | |
| | 0 | 1 | 2 | 3 | 4 | 5 | 6 | Total |
|---|---|---|---|---|---|---|---|---|
| OZA* | 5 | 2 | 1 | 1 | 0 | 0 | 0 | 9 |
| NOV* | 1 | 1 | 2 | 1 | 0 | 3 | 0 | 8 |

TABLE 2-continued

| | Grade | | | | | | | |
| | 0 | 1 | 2 | 3 | 4 | 5 | 6 | Total |
|---|---|---|---|---|---|---|---|---|
| Antithrombotic agent alone | 6 | 3 | 3 | 2 | 0 | 3 | 0 | 17 |
| Edaravone + OZA* | 2 | 1 | 0 | 1 | 1 | 0 | 1 | 6 |
| Edaravone + NOV* | 9 | 1 | 2 | 0 | 0 | 2 | 0 | 14 |
| Edaravone + antithrombotic agent | 11 | 2 | 2 | 1 | 1 | 2 | 1 | 20 |

*OZA means sodium ozagrel and NOV means argatroban.

In the above-described table, what the meaning of grade will be explained briefly. Grade 0: no symptoms, Grade 1: some symptoms but non-significant disability (able to carry out all daily activities and affairs), Grade 2: slight disability (unable to carry out all previous activities but able to look after own affairs without assistance), Grade 3: moderate disability (requiring some help, but able to walk without assistance), Grade 4: relatively severe disability (requiring assistance for walk or daily activities), Grade 5: very severe disability (bedridden, incontinence and requiring constant nursing care and attention), Grade 6: death.

Comparative Example

Evaluation results of edaravone, when administered alone, in accordance with the modified ranking scale are included in Therapeutic Research, Vol. 19(4), 1333-1345, 1998.

Evaluation method and results: Edaravone (30 mg/20 ml) diluted with 100 ml of physiological saline was intravenously infused to 8 patients in the acute stage of cerebral infarction constantly for 14 days twice daily (morning and evening), each over 30 minutes. During the administration term of this medicament, administration of another medicament which might have an influence on the drug efficacy evaluation was avoided. Evaluation was made in accordance with the modified ranking scale three months after the initiation of the administration or upon discharge of the patient from the hospital within three months after the initiation of administration. Results are as shown below.

| | Grade | | | | | | | |
| | 0 | 1 | 2 | 3 | 4 | 5 | 6 | Total |
|---|---|---|---|---|---|---|---|---|
| Administration of edaravone alone | 0 | 2 | 3 | 0 | 3 | 0 | 0 | 8 |

Grade 1: Some symptoms but non-significant disability
Grade 2: Slight disability
Grade 4: Relatively severe disability There is no difference between Example and Comparative Example except for the time of evaluation based on the modified ranking scale, that is, within one month after the initiation of administration in Example, while within three months in Comparative Example. These results obtained in Example and Comparative Example were therefore compared, which has revealed that a ratio of Grade 0 was 35.3% when the antithrombotic agent was used alone and 0% when edaravone was used alone, while it was 55.0% when the antithrombotic agent and edaravone were used in combination. This suggests that combined use of the antithrombotic agent and edaravone brings not merely an additive effect but a synergistic effect, and function prognosis is good.

INDUSTRIAL APPLICABILITY

By combining of antithrombotic agent, the pyrazolone derivatives used in the present invention can enhance the suppressing effects to the function disorder of the antithrombotic agent, suppress the aggravate of the symptoms caused by the side effects of the antithrombotic agent and reperfusion injuries to a minimum, and then bring the more safe clinical effects.

The combined drugs of the present invention are useful as the preventive and/or remedial medicament for various ischemic diseases or various diseases caused thereby, specifically various cerebral diseases, for example, cerebrovascular disorders such as cerebral infarction and stroke, impairment of brain functions due to these cerebrovascular disorders, vascular dementia, age-related damage to cerebrovascular tissues; various heart diseases caused by myocardial ischemia such as myocardial infarction and cardiac failure; and various peripheral circulatory disorders.

All of the contents described in the specifications of Japanese Patent Application No. 2001-279645 and Japanese Patent Application No. 2001-365032 which are claiming the priority and are the basic patent applications of the present patent application can be incorporated by reference into the present specification as a part of the disclosure of the present specification.

The invention claimed is:

1. A method of treating an ischemic disease selected from cerebral infarction, stroke, and impairment of brain function due to cerebral infarction or stroke in a patient comprising parenterally administering to the patient in need thereof and having an ischemic disease selected from cerebral infarction, stroke, and impairment of brain function due to cerebral infarction or stroke
   (a) a dose of about 0.6 mg per kg of patient weight of a tissue plasminogen activator, and
   (b) a dose of 60 mg per day of 3-methyl-1-phenyl-2-pyrazolin-5-one or a pharmaceutically acceptable salt thereof,
   whereby the ischemic disease is treated in the patient.

2. The method according to claim 1, wherein the tissue plasminogen activator and the 3-methyl-1-phenyl-2-pyrazolin-5-one or pharmaceutically acceptable salt thereof are administered simultaneously.

3. The method according to claim 1, wherein the ischemic disease is cerebral infarction or stroke.

4. The method according to claim 1, wherein the ischemic disease is characterized by nerve symptoms, daily behavior problems, or functional disturbances in the acute stage of cerebral infarction.

5. The method according to claim 1, wherein the tissue plasminogen activator and the 3-methyl-1-phenyl-2-pyrazolin-5-one or pharmaceutically acceptable salt thereof are administered separately.

6. The method according to claim 1, wherein the tissue plasminogen activator is administered after the administration of the 3-methyl-1-phenyl-2-pyrazolin-5-one or pharmaceutically acceptable salt thereof.

* * * * *